(12) United States Patent
Taylor (10) Patent No.: US 8,497,119 B1
(45) Date of Patent: Jul. 30, 2013

(54) METHOD AND DEVICE FOR PERFORMING MICRO-OPERATIONS ON A VESICULAR OBJECT

(76) Inventor: Paul J. Taylor, Bozeman, MT (US)

( * ) Notice: Subject to any disclaimer, the term of this patent is extended or adjusted under 35 U.S.C. 154(b) by 0 days.

(21) Appl. No.: 13/374,195

(22) Filed: Dec. 14, 2011

Related U.S. Application Data (60) Provisional application No. 61/459,577, filed on Dec. 15, 2010.

(51) Int. Cl.
  *C12M 5/00* (2006.01)
  *C12M 15/00* (2006.01)
  *C12M 3/00* (2006.01)

(52) U.S. Cl.
  USPC .......................... 435/325; 435/470; 435/287.3

(58) Field of Classification Search
  None
  See application file for complete search history.

(56) References Cited

U.S. PATENT DOCUMENTS

| | | | |
|---|---|---|---|
| 4,619,899 | A | 10/1986 | Nikitin et al. |
| 5,114,854 | A | 5/1992 | Bertholdt |
| 5,877,008 | A | 3/1999 | Remenyik et al. |
| 6,592,552 | B1 | 7/2003 | Schmidt |
| 7,855,067 | B2 | 12/2010 | Sasaki et al. |

*Primary Examiner* — Ruth Davis
*Assistant Examiner* — Emily Cordas (57) ABSTRACT

A method for performing micro-operations on a vesicular object comprising securing the vesicular object by applying negative pressure in a radial vacuum passage; advancing a pipette into the vesicular object through an axial vacuum passage; ensuring that the axial vacuum passage and the radial vacuum passage are not in fluid contact with each other; controlling the negative pressure in both axial and radial vacuum passages, and the pressure or vacuum in the pipette separately; whereby allowing the simultaneous holding of the vesicular object by applying negative pressure in the radial vacuum passage; injection into or aspiration from the vesicular object via the pipette; and aspiration from the vesicular object by applying negative pressure in the axial vacuum passage.

1 Claim, 8 Drawing Sheets

METHOD AND DEVICE FOR PERFORMING MICRO-OPERATIONS ON A VESICULAR OBJECT

CROSS-REFERENCE TO RELATED APPLICATIONS

This application claims the benefit of PPA Ser. No. is 61/459,577 filed Dec. 15, 2011 by the present inventor, which is incorporated by reference.

FEDERALLY SPONSORED RESEARCH

This invention was not made under a government contract and the government has no rights in it.

SEQUENCE LISTING OR PROGRAM

Not applicable.

BACKGROUND—PRIOR ART

The following is a tabulation of some prior art that presently appears relevant:

U.S. PATENTS

| Pat. No. | ISSUE DATE | PATENTEE |
| --- | --- | --- |
| 4,619,899 | October 1986 | Nikitin, et al. |
| 5,114,854 | May 1992 | Bertholdt |
| 5,877,008 | March 1999 | Remenyik, et al. |
| 6,592,552 B1 | July 2003 | Schmidt |
| 7,855,067 B2 | December 2010 | Sasaki, et al. |

FOREIGN PATENT DOCUMENTS

FOREIGN Doc. NR.
10-2005-0023483
WO 2009/070474 A1

NON-PATENT LITERATURE DOCUMENTS http://www.eppendorf.com/int/img/na/lit/pdf8301-C110G-07.pdf

BACKGROUND

The present method and device relates to a method and device for manipulating the contents of a vesicular object having a size typically in the neighborhood of 100-300 microns. This method and device has particular application for manipulation of the contents of mammalian embryos at the hatched blastocyst stage of development. This has not been possible with any previous device.

Working with the hatched blastocyst has been difficult because the blastocysts are spherical vesicular structures consisting of a thin double layer of living cells surrounding a relatively large central cavity that is filled with an aqueous fluid. The difficulty, and the failure of the prior art, arises because of the physical characteristics of the envelope of these living cells which is flimsy but very resistant to puncture. For example, trying to inject material into a hatched blastocyst often simply pushes in the membrane without puncturing it, or conversely, ends up destroying the integrity of the membrane altogether. This compression can be severe and potentially damaging to the living cells. With the present device there is no compression at all.

Additionally, conventional methods disclosed by the prior art require a holding pipette on one side, and a separate injection pipette on the opposite side, with expensive micromanipulators for positioning of these two pipettes in 3-axes so they are perfectly aligned for puncture of the vesicular object. Because the forces pushing the oocyte and the pipette together have to be exactly aligned for penetration, both the holding and injection pipettes, presented from above, must have a 30 degree bend near the tip so they can be parallel to the floor of the dish and to each other. None of this is necessary with the present device.

ADVANTAGES OF THE EMBODIMENT

The present method and device overcomes the above-described difficulties by providing a method and device which, using vacuum, firmly holds a portion of the surface of the blastocyst prior to piercing. Due to the method and device's unique double vacuum passages, fluid can be injected into a vesicular object while contained fluid is simultaneously, and rapidly, extracted from it. This rapid extraction provides the additional benefit of allowing the object's total volume to be held constant, preventing damage to early embryos that cannot tolerate complete collapse. As used herein, use of the word "fluid" includes any solids, including for example, DNA or other genetic material, associated with that fluid.

The method and device provides secure holding of a portion of the surface, especially the surface of a hatched blastocyst, for injection into the central volume of liquid, or reduction of that central volume, either through the pipette or around the pipette through the opening in the distal end of the inner tip.

Only this method and device offers the capability for simultaneous injection and aspiration, which allows the composition of the central volume to be changed rapidly without a change in total volume. That is crucial to freezing of large vesicular structures that cannot tolerate collapse, such as the horse hatched blastocyst or the zebrafish embryo, neither of which have ever been successfully frozen.

These and other advantages of one or more aspects of the method and device will become apparent from a consideration of the ensuing description and accompanying drawings.

SUMMARY, CONCLUSION, RAMIFICATIONS, AND SCOPE

The above-described method and device, using vacuum, firmly holds a portion of the surface of the blastocyst for puncture. Due to the present method and device's unique double vacuum passage, fluid can be injected into the vesicular object while fluid is simultaneously extracted from that vesicular object.

The method and device allows for the above-described procedures to be done with the widely available stereoscope thereby expanding the number of facilities capable of performing many procedures.

In the future, there may be increased sophistication of the micromanipulation capabilities for movement of the pipette, integrated into the device itself. This embodiment will be for use on smaller embryos and usually used with inverted microscopes. It will likely include the capability for rapid forward and back oscillation of the pipette by a few microns, resulting in a piezo hammer or impact drill effect, for easy penetration of hard objects like the zona pellucida of the oocyte and early embryo.

REFERENCE NUMERALS

1. Outer Assembly
2. Vacuum Jacket
3. Radial Vacuum Port
4. Axial Vacuum Port
5. Inside of Vacuum Jacket
6. Male Threads on Outer Surface of Vacuum Jacket
7. Outer Tip
8. Primary Aperture
9. Barrel Assembly
10. Upper Barrel
11. External Threads on Upper Barrel and Vacuum Jacket
12. Coupling
13. Knurled Outer Surface of Coupling
14. Internal Threads on Inner Surface of Coupling
15. Internal Threads in Upper Barrel
16. External Threads on Lower Barrel
17. Inner Seal
18. Lower Barrel
19. Groove for Proximal O-ring
20. Proximal O-ring
21. Shunt
22. Groove for Distal O-ring
23. Distal O-ring
24. Nipple of Lower Barrel
25. Ferrule
26. Inner Tip
27. Pipette
28. Open Tip of Pipette
29. Axial Vacuum Passage
30. Radial Vacuum Passage
31. Holding Well
32. Secondary Aperture
33. Central Bore
34. Vesicular Object

DETAILED DESCRIPTION OF AN EMBODIMENT

Elements

Figure 1:
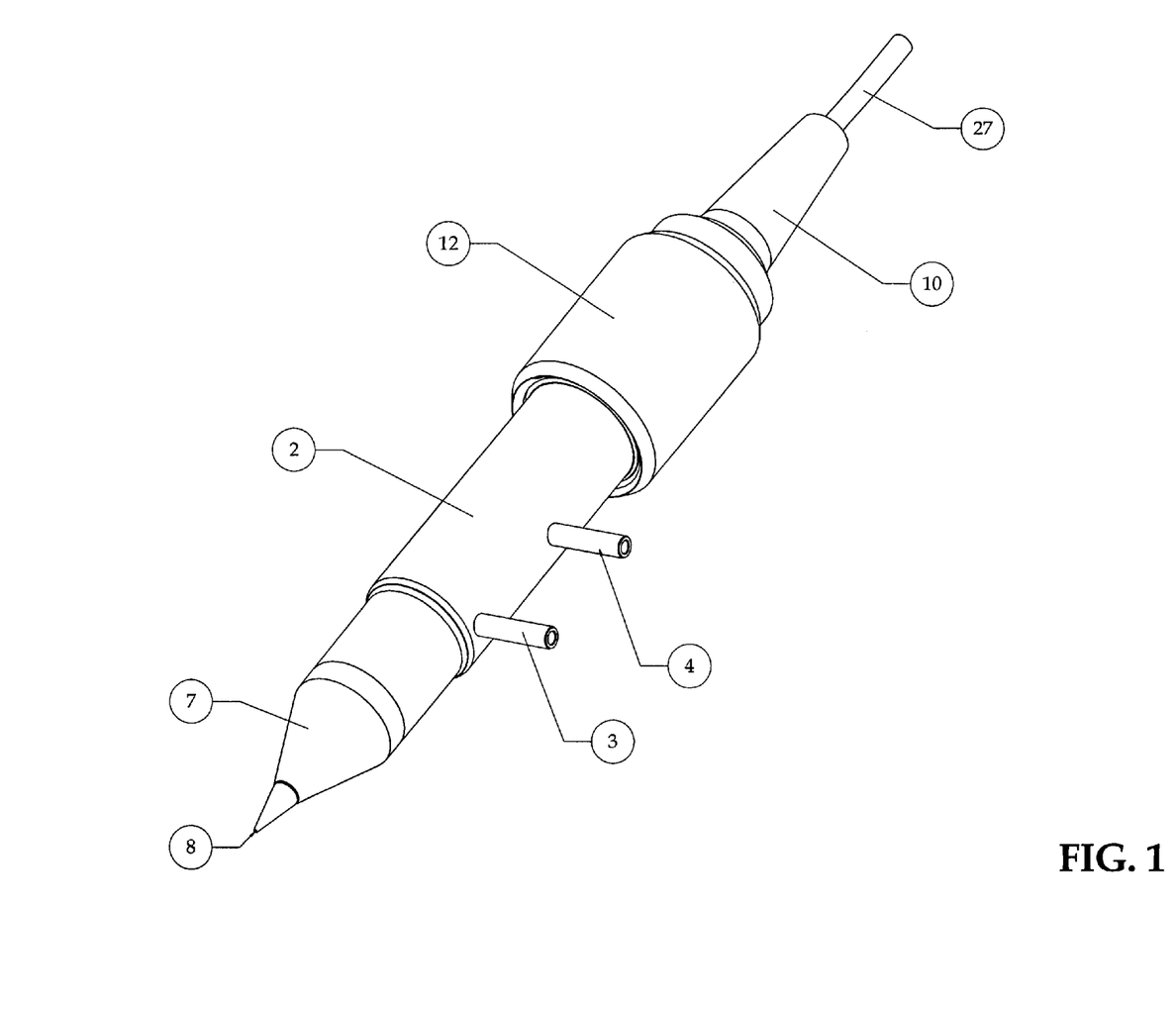
FIG. 1 is a perspective view of the device.
Figure 7:
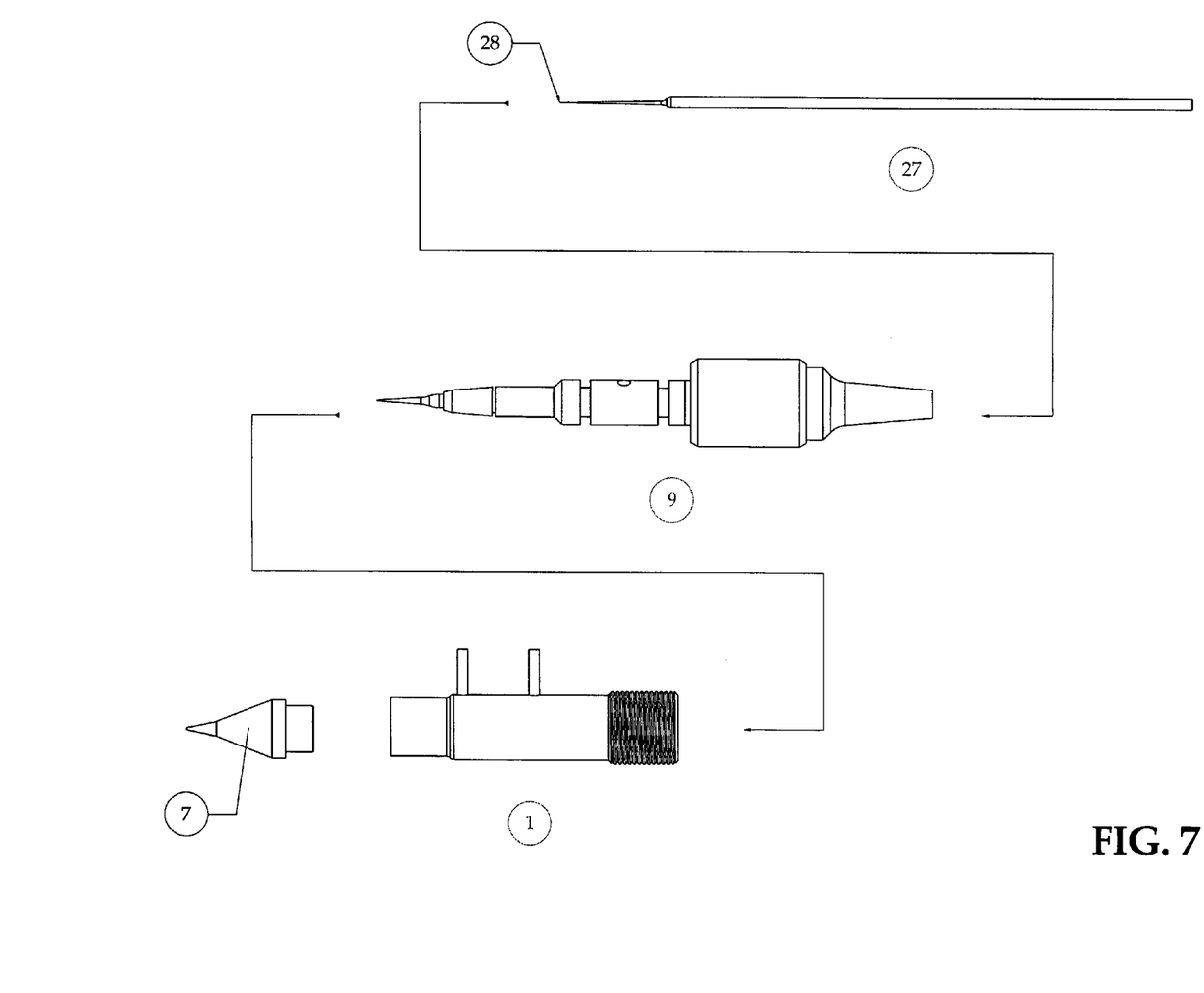
FIG. 7 is an assembly diagram of the components of the device shown in FIG. 1.

A device for performing micro-operations on a vesicular object is shown in FIG. 1. In this embodiment, in addition to a pipette (27) capable of injection and aspiration through an opening in its distal end (28), the device includes two separate generally cylindrical assemblies. The first assembly is an outer assembly (1) and the second assembly is a barrel assembly (9). The barrel assembly (9) is inserted into the outer assembly (1) as shown in FIG. 7.

Outer Assembly

Figure 5:
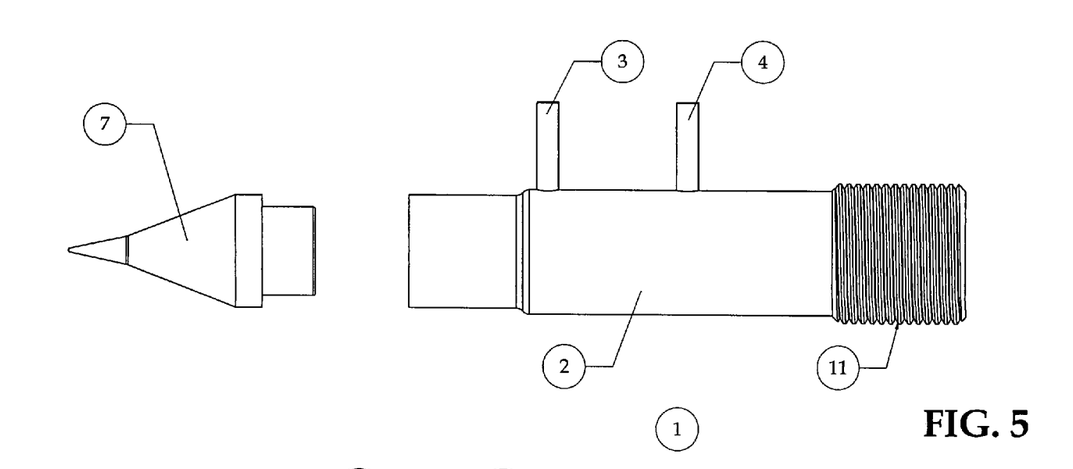
FIG. 5 is an enlarged elevational view of the vacuum jacket and outer tip.
Figure 6:
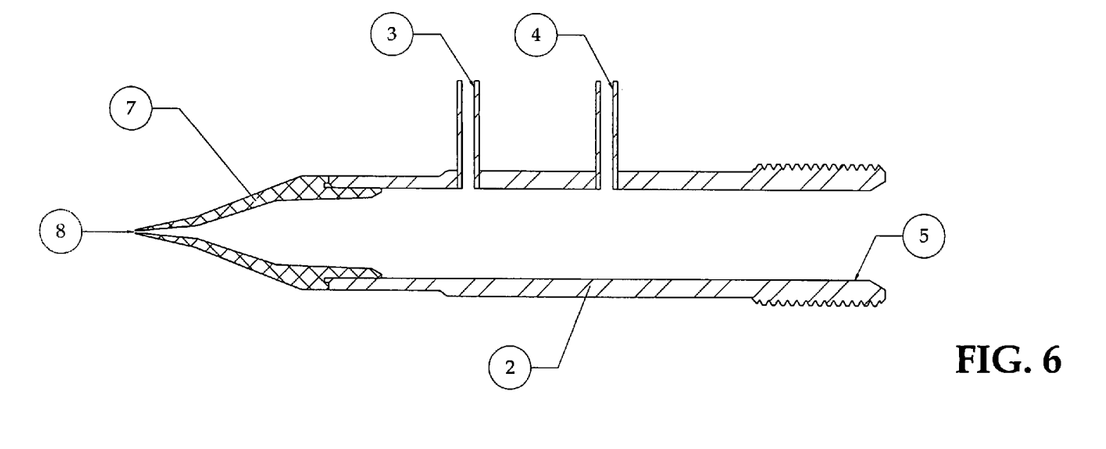
FIG. 6 is an enlarged cross-sectional view of the assembled vacuum jacket and outer tip shown in FIG. 5.
Figure 9:
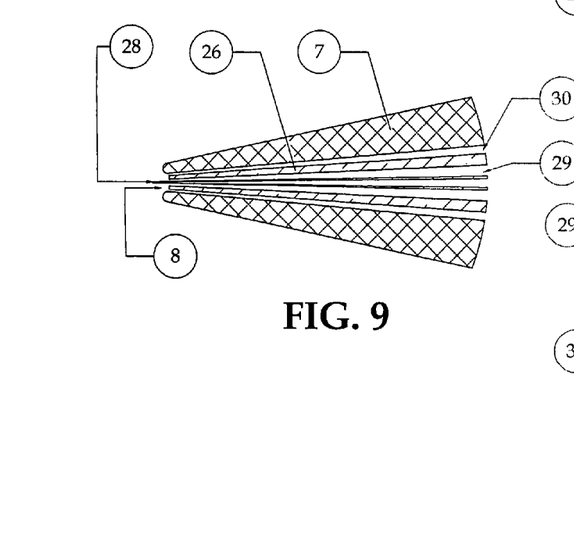
FIG. 9 is a detail view at "A" shown in FIG. 8.

The outer assembly comprises a vacuum jacket and an outer tip. FIG. 5. The vacuum jacket (2) includes a main body portion open at both ends. A conical outer tip, FIG. 5 (7) is frictionally fitted at one end of the vacuum jacket (2) as shown in FIG. 6. The inside diameter of the outer tip at its distal end (7) defines an opening, the primary aperture (8). FIGS. 1 and 9.

Figure 2:
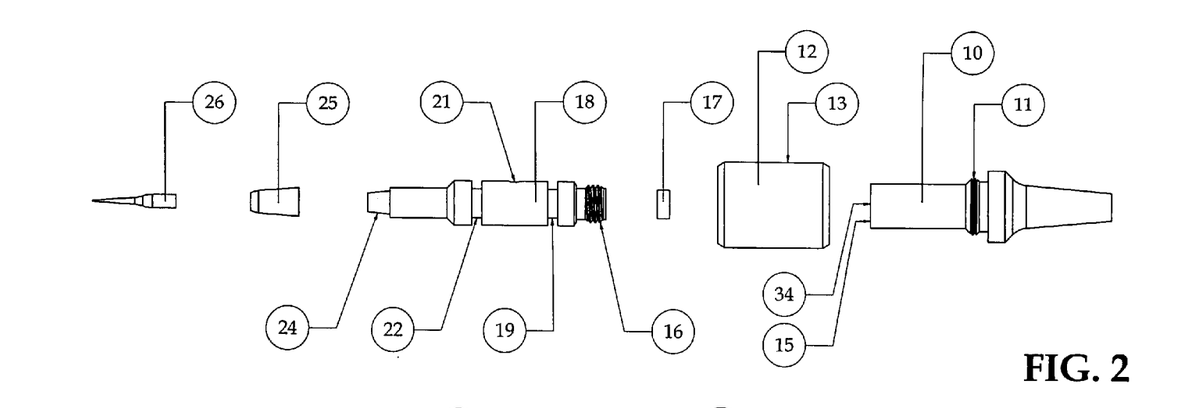
FIG. 2 is an elevational exploded view of the components of the barrel assembly used with the present device.
Figure 3:
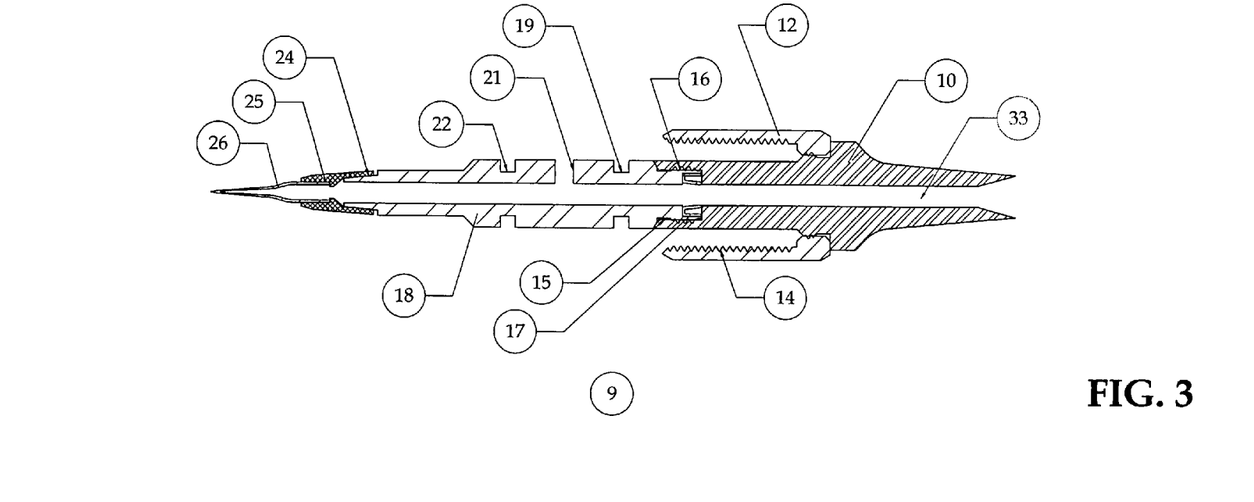
FIG. 3 is an enlarged cross-section view of a barrel assembly used with the present device.

The vacuum jacket (2) is provided with external threads FIG. 5 (11) at its proximal end, for threadably engaging internal threads FIG. 3 (14) provided inside a rotatable coupling FIG. 2 (12) such coupling being attached to the upper barrel FIG. 2 (10) by means of external threads (11) on the upper barrel (10). The knurled outer surface (13) of the coupling (12) allows the user to easily thread the barrel assembly (9) into the vacuum jacket FIG. 7. The vacuum jacket is also provided with a radial vacuum port FIG. 6 (3) and an axial vacuum port (4) both of which extend through the wall of the vacuum jacket (2). These vacuum ports provide fluid communication to the interior of the vacuum jacket.

Barrel Assembly

Figure 4:
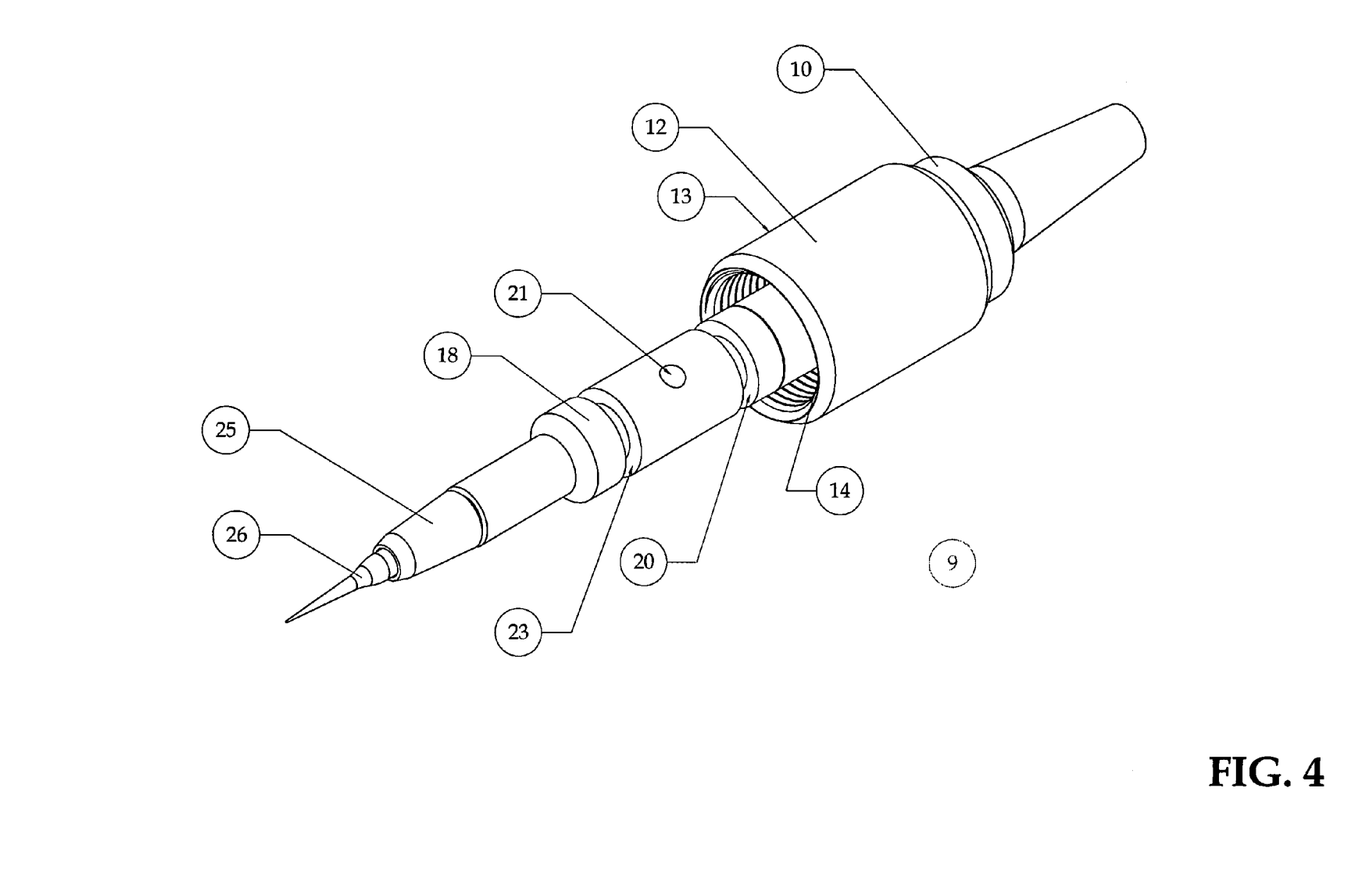
FIG. 4 is a perspective view of the barrel assembly used with the present device.

In this embodiment the barrel assembly FIG. 4 (9) includes an upper barrel (10), a lower barrel (18), a rotatable coupling (12), a spring-energized inner seal positioned between the upper and lower barrel FIG. 3 (17), a ferrule (25), and an inner tip (26). The upper barrel (10) is provided with a blind bore for threadably receiving the lower barrel (18) as shown in FIG. 3. The lower barrel (18) has external threads (16) for mating with internal threads (15) located within the blind bore provided at the distal end of the upper barrel (10) as shown in FIG. 3. The proximal end of the lower barrel has, inside its threaded end, a blind bore for seating of the inner seal (17). Both the lower barrel (18) and the Upper barrel (10) are provided with co-aligned axial bores forming a central bore. FIG. 3. (33).

Figure 8:
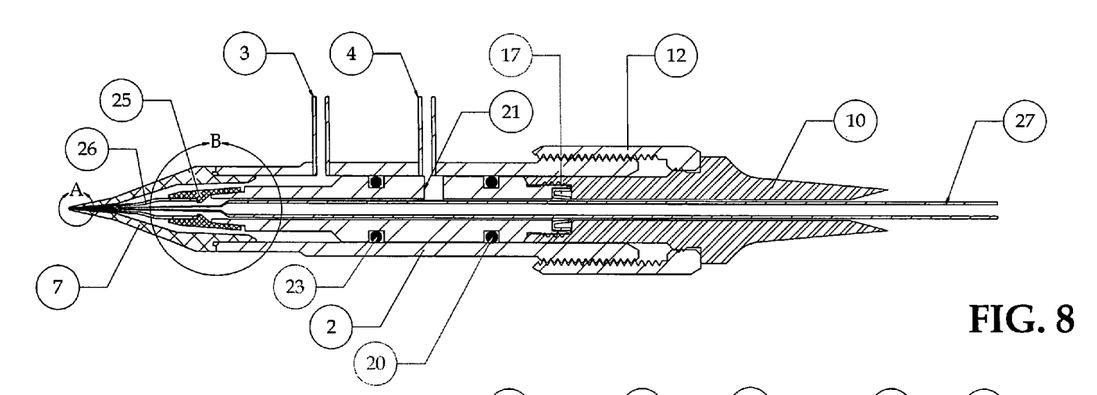
FIG. 8 is an enlarged cross-section of the device shown in FIG. 1.
Figure 10:
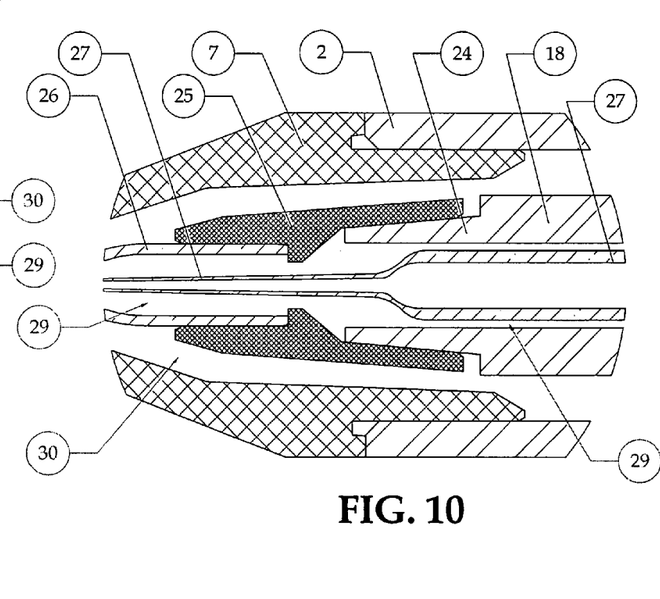
FIG. 10 is a detail view at "B" shown in FIG. 8.
Figure 11:
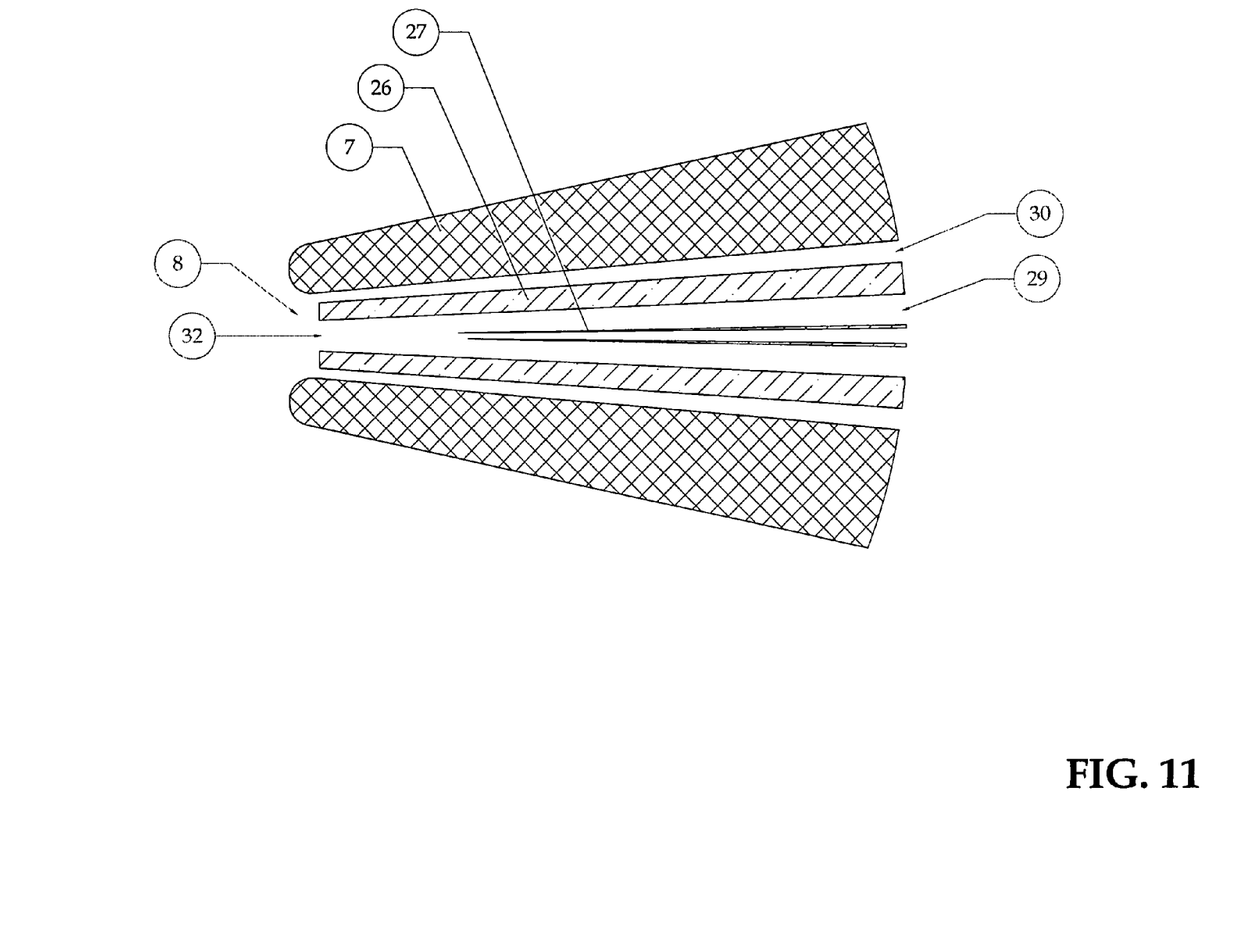
FIG. 11 is a detail cross-sectional view of the distal end of the device (the tip) shown in use, with the pipette withdrawn.

A pipette FIG. 7 (27) is slidably received by the axial bores. The axial bores are sized to leave an axial vacuum passage FIG. 10 (29) between the pipette (27) and the lower barrel (18). FIG. 10. Such axial vacuum passage extending along the pipette and terminating at the secondary aperture. FIG. 11. (32). The pipette (27) includes a tapered needle end and opening (28) at its distal end. FIG. 9. A spring-energized lip seal, the inner seal (17), is used to seal the lower barrel (18) against the pipette (27). FIG. 8. The distal end of the lower barrel (18) is further provided with a cylindrical portion having a reduced outside diameter as shown in FIGS. 2 and 3. The outside diameter of the cylindrical portion is less than the inside diameter of the outer tip (7) as shown in FIG. 10 to provide a radial vacuum passage (30) terminating between the inside of the outer tip (7) and outside of the inner tip (26) as shown in FIGS. 10 and 11.

In this embodiment, the distal end of the lower barrel (18) is a metal nipple (24) designed to fit, via self-locking taper, into a stopped bore at the proximal end of a plastic ferrule FIG. 2 (25). The proximal end of the inner tip (26) is frictionally fitted into a stopped bore at the distal end of the ferrule (25) as detailed in FIGS. 2 and 3. The inner tip (26) open at both ends, functions as a guide when the needle end (28) of pipette is extended through the secondary aperture at the distal end of the inner tip FIG. 11 (32).

The ferrule FIG. 2 (25) provides a positive seal between the lower barrel nipple FIG. 2 (24) and the inner tip (26) while also providing a flexible joint to insure the inner tip (26) can align concentrically within the primary aperture (8) of the outer tip FIG. 8 (7) during use. The lower barrel (18) is also provided with grooves (19) and (22) as shown in FIG. 2 for receiving O-rings (20) and (23) as shown in FIG. 8.

The lower barrel (18) is also provided with a shunt FIG. 8 (21) that places the axial vacuum port (4) in fluid communication with the portion of the axial vacuum passage (29) surrounding the pipette (27). FIG. 10.

Interrelationship of Elements

As shown in FIGS. 8 through 10, when a vacuum is applied through the radial vacuum port (3) the vacuum is in fluid communication with the radial vacuum passage (30). When a vacuum is applied to the axial vacuum port (4), the vacuum is in fluid communication, by means of the shunt (21), with the axial vacuum passage (29), such passage extending from the shunt, distally along the pipette, and terminating at secondary aperture FIG. 11. (32).

Figure 12:
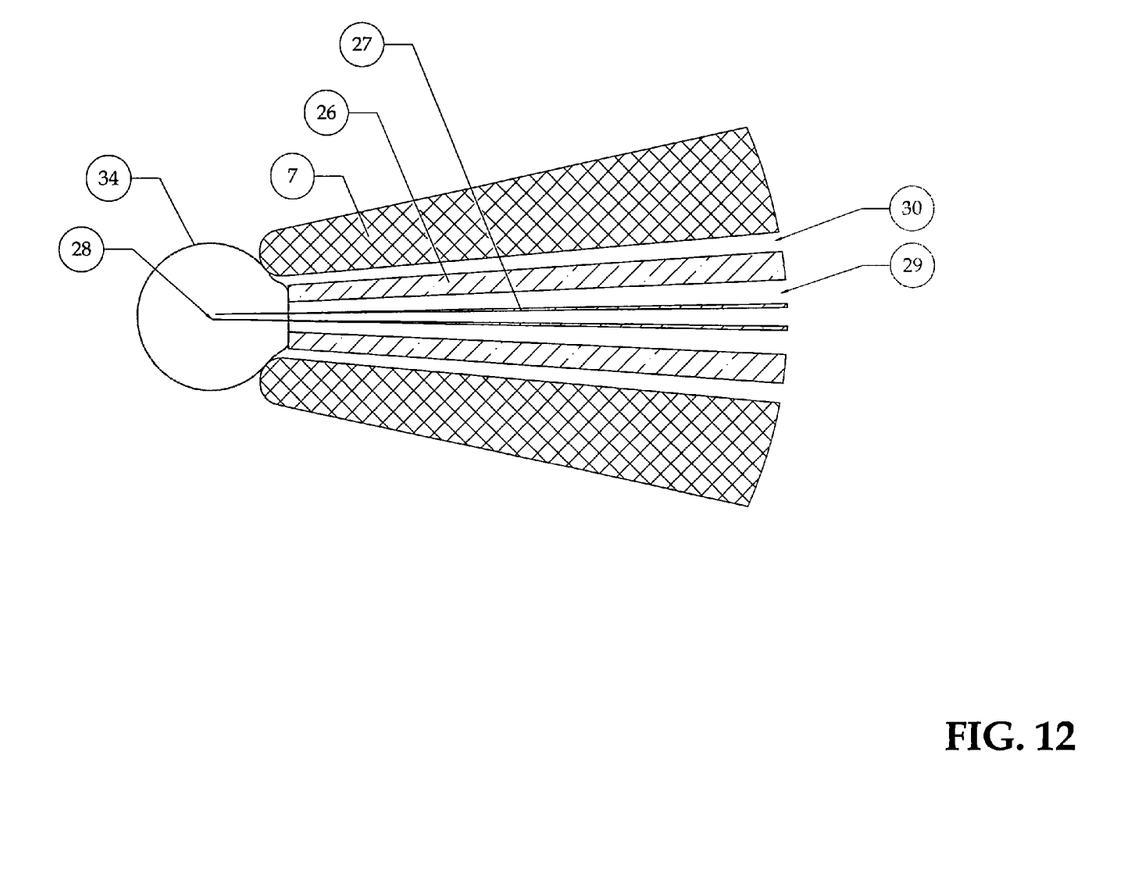
FIG. 12 is a detail cross-sectional view of the distal end of the device (the tip) shown in use, with the pipette advanced and having pierced a vesicular object.

As shown in FIG. 9), the position of distal end of the inner tip (26) in relation to the distal end of the outer tip (7), is adjusted with the threaded coupling (12) connecting the vacuum jacket (2) and the barrel assembly (9). FIG. 8. This provides, and determines the shape of, a holding well (31), formed by the combination of inner and outer tips at the distal end of the device, for holding a vesicular object such as an embryo or other vesicular structure. FIGS. 11 and 12.

Operation

1. As shown in FIG. 7, in operation of the present embodiment, the barrel assembly (9) is inserted through the opening in the proximal end of the outer assembly (1) and, by rotation, the threaded coupling (12) on the barrel assembly is used to advance or withdraw the distal end of the inner tip (26) in relation to the distal end of the outer tip to form the desired contour of the holding well (31) as shown in FIG. 11.

2. A pipette (27) is slidably inserted through the bores provided in the barrel assembly (9), passing through the inner seal (17). The pipette (27) is slidably adjusted so that the needle end (28) of the pipette (27) is slightly retracted from the inner tip opening, the secondary aperture (32). FIG. 11. A vesicular object, such as a blastocyst, is positioned immediately in front of the primary aperture (8) of the outer tip (7) as shown in FIG. 12.

3. A vacuum source (not shown) is connected to the radial vacuum port (3) and a second vacuum source (not shown) is connected to the axial vacuum port (4). FIG. 8. With vacuum applied to the radial vacuum port (3), vacuum through the radial vacuum passage (30) securely holds the vesicular object within the holding well formed at the primary aperture (8).

4. The final position of the inner tip (26) may then be advanced or withdrawn as needed to produce the desired relation with the surface of the vesicular object using the threaded coupling (12) so that the inner tip rests against, and seals against, the secured object. FIG. 12. At which point the vacuum in passage (30) acts only on the ring of the vesicular object's surface in the area (30) between the distal end of the inner tip (26) and the distal end of the outer tip (7). FIG. 12.

5. Vacuum can be applied to the axial vacuum port (4) and thereby to axial vacuum passage (29), to draw the exact point of penetration of the vesicular object surface tightly against the secondary aperture (32) in the distal end of the inner tip at the moment of penetration. FIG. 12.

6. The needle end (28) of the pipette (27) may then be slidably extended to pierce the outer surface of the vesicular object. FIG. 12.

7. Fluid can then be injected into, or aspirated from, the vesicular object through the pipette (27).

8. Vacuum can be applied to the axial vacuum port FIG. 8 (4) and thereby to axial vacuum passage (29), to draw fluid from the central volume of the object through the secondary aperture (32), that is, from between the inside of the inner tip (26) and the outside of the needle end (28) of the pipette (27). FIG. 12.

9. With this procedure, it is possible to inject or withdraw fluid into the central volume of the vesicular object via the pipette (see Step 7 above) and also aspirate from the central volume of the vesicular object via the secondary aperture (see Step 8 above) simultaneously.

10. Another effect of the vacuum applied to the axial vacuum port (4) is to draw the external surface of the vesicular object taut across the secondary aperture (32), and allow for easy puncture with the needle end (28) of the pipette (27) as shown in FIG. 12.

This apparatus has particular advantage when working with a hatched blastocyst where the external surface of the embryo is very flimsy so it cannot be held on one side and punctured from the opposite side.

While the above description contains many specificities, these should not be construed as limitations on the scope of any embodiment, but as examples of various embodiments thereof. Many other ramifications and variations are possible within the teachings of the various embodiments without departing from the scope of the method and device disclosed above.

Thus the scope should be determined by the appended claims and their legal equivalents, and not by the examples given.

I claim:

1. A method for performing micro-operations on a vesicular object by:
    a) securing the vesicular object by applying negative pressure in a radial vacuum passage (30) such radial vacuum passage including being a passage between an outer tip (7) and an inner tip (26), and such passage terminating at a primary aperture (8);
    b) advancing a pipette (27), such pipette being capable of injection or aspiration through an opening at its distal end (28), through an axial vacuum passage, such axial vacuum passage including being a passage between the inner tip and the distal end of the pipette, such passage terminating at a secondary aperture (32);
    c) penetrating the secured vesicular object at the secondary aperture (32);
    d) ensuring that the axial vacuum passage and the radial vacuum passage are not in fluid contact with each other or with atmospheric pressure;
    e) controlling the negative pressure in both axial and radial vacuum passages, and the pressure in the pipette, separately;
    whereby allowing the simultaneous holding of the vesicular object at the primary aperture by applying negative pressure in the radial vacuum passage; injection into or aspiration from the vesicular object via the pipette; and aspiration from the vesicular object at the secondary aperture by applying negative pressure in the axial vacuum passage.

* * * * *